United States Patent
Bellini et al.

(10) Patent No.: US 7,437,897 B2
(45) Date of Patent: Oct. 21, 2008

(54) DYEING MACHINE WITH AUTOMATIC IN-LINE DIP DEPLETION CONTROL

(75) Inventors: Giovanni Bellini, Milanese (IT); Giuseppe Meneghello, Recoaro Terme (IT); Marco Rossi, Vicenza (IT)

(73) Assignee: Dyecontrol By Loris Bellini E. Zaitex S.r.l. (IT)

( * ) Notice: Subject to any disclaimer, the term of this patent is extended or adjusted under 35 U.S.C. 154(b) by 553 days.

(21) Appl. No.: 10/515,122

(22) PCT Filed: May 20, 2003

(86) PCT No.: PCT/EP03/05285

§ 371 (c)(1), (2), (4) Date: Nov. 16, 2004

(87) PCT Pub. No.: WO03/102288

PCT Pub. Date: Dec. 11, 2003

(65) Prior Publication Data

US 2005/0172679 A1 Aug. 11, 2005

(30) Foreign Application Priority Data

May 31, 2002 (IT) .......................... MI2002A1192

(51) Int. Cl.
*D06B 23/28* (2006.01)

(52) U.S. Cl. .................... 68/13 R; 68/181 R; 68/184

(58) Field of Classification Search ............... 68/13 R, 68/181 R, 184
See application file for complete search history.

(56) References Cited

U.S. PATENT DOCUMENTS

| | | | | |
|---|---|---|---|---|
| 3,088,479 A | * | 5/1963 | Christie ....................... 137/93 |
| 3,807,872 A | * | 4/1974 | Pronier ....................... 356/410 |
| 3,867,040 A | * | 2/1975 | Loffler et al. ............... 356/410 |
| 3,890,510 A | * | 6/1975 | Sturm ......................... 250/565 |
| 4,089,644 A | * | 5/1978 | Carbonell et al. ............. 8/400 |
| 4,152,113 A | * | 5/1979 | Walker et al. ................. 8/440 |
| 4,374,322 A | * | 2/1983 | Hoffmann et al. ........... 250/226 |
| 5,001,938 A | * | 3/1991 | Downie ................... 73/864.34 |
| 5,072,472 A | * | 12/1991 | Enderlin ..................... 8/151.2 |
| 5,115,874 A | * | 5/1992 | Hayahara et al. .............. 177/70 |
| 5,287,168 A | * | 2/1994 | Poucher et al. ............. 356/436 |
| 5,687,589 A | * | 11/1997 | Yao et al. .................. 68/12.07 |

(Continued)

FOREIGN PATENT DOCUMENTS

FR 319 361 * 6/1989

(Continued)

*Primary Examiner*—Frankie L Stinson
(74) *Attorney, Agent, or Firm*—Shlesinger & Fitzsimmons

(57) ABSTRACT

A dyeing machine comprises a container (11) in which products to be dyed are placed, a source (12) of coloring liquids adding liquids on command into the container to realize a dye dip, and a unit (13) to circulate the dye dip with respect to the product. During the dyeing process a sampling and analysis device (14) automatically takes samples of liquid from the container at intervals and performs a spectroscopic analysis thereon. An electronic control and calculation device (15) receives the spectroscopic analysis data and calculates therefrom the concentrations of the various dyestuffs in the dip. The behavior thus obtained of the dip can be memorized for future use and/or can be used to command appropriate corrective parameters of the dyeing process.

15 Claims, 1 Drawing Sheet

U.S. PATENT DOCUMENTS

Figure 1:
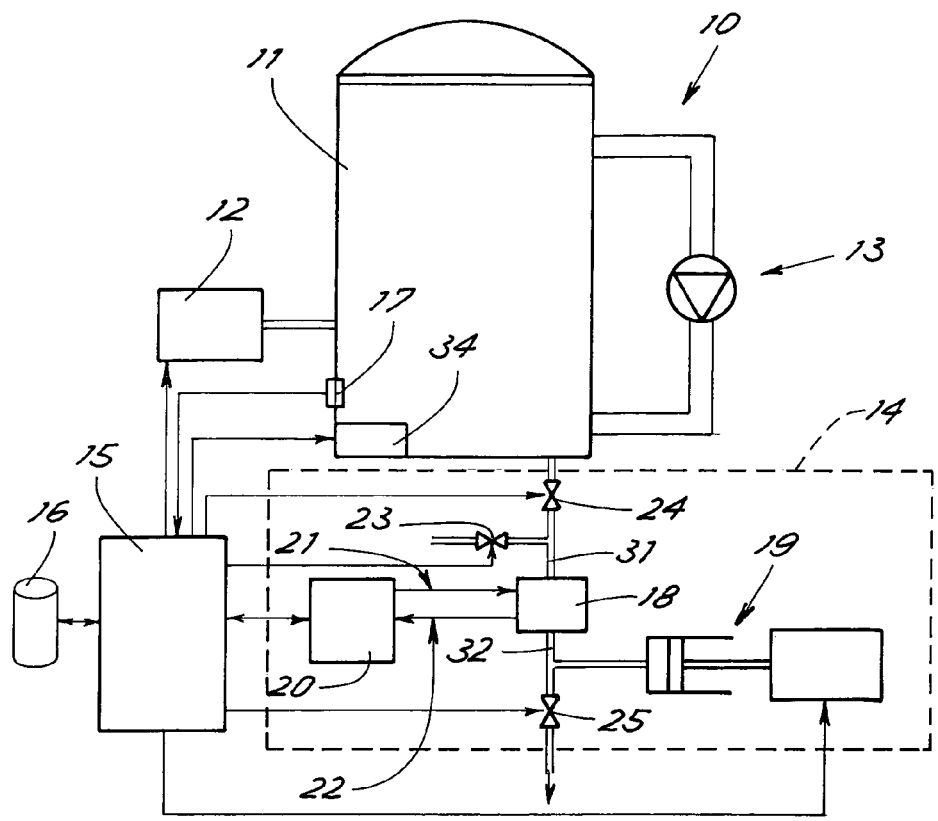

| | | | | |
|---|---|---|---|---|
| 6,056,790 A | * | 5/2000 | Clark et al. | 8/502 |
| 6,221,112 B1 | * | 4/2001 | Snider | 8/470 |
| 6,507,397 B1 | * | 1/2003 | Nishio et al. | 356/319 |
| 6,615,620 B2 | * | 9/2003 | Hendrix et al. | 68/207 |
| 6,917,424 B2 | * | 7/2005 | Rodrigues et al. | 356/326 |

FOREIGN PATENT DOCUMENTS

| | | | |
|---|---|---|---|
| FR | 631 119 | * | 6/1994 |
| GB | 1 295 620 | * | 5/1975 |
| GB | 1 395 620 | * | 5/1975 |

* cited by examiner

DYEING MACHINE WITH AUTOMATIC IN-LINE DIP DEPLETION CONTROL

The present invention relates to a dyeing machine capable of automatically recording dye concentrations in the dye dip during the process, testing their trend over time and if necessary changing it by acting on appropriately chosen control parameters, for example temperature, pH and so on. The machine is designed in particular but not exclusively for textile products.

In the prior art of dying machines the importance of the so-called 'formula', that is to say the composition of the dye dip, to achieve optimal results is well known.

Usually, dye dips are made from a composition of several dyestuffs and if necessary additives in solution or aqueous dispersion or with solvents. During the dyeing process the various dyestuffs are often absorbed at different speeds by the product being dyed. When one of the dyestuffs is no longer present in the dip in sufficient quantity the dip is depleted. It is therefore important to known the evolution of the dip during the process to be able to optimize the dip formula and to ensure good execution of the process.

In the known art, a series of samplings of the dye liquid are usually made at intervals during a process and the samples are analyzed in a laboratory to go back to the dynamics of the concentrations of the various dyes during the process. Since this operation is costly in terms of time and money, it is generally performed only for one or a few initial sample processes in order to optimize the dip formula and the application methodology for subsequent in-line processing. During normal in-line dyeing processes dip analysis is no longer performed or is performed rarely while trusting that the dip will always hold the same behavior found at the beginning.

Unfortunately, the course of the dyestuff concentrations depends in reality on various parameters such as temperature, pH, salinity, auxiliary product quantities, circulation pump speed et cetera.

It has been proposed to monitor the behavior of the colors in the dye dip by using colored filters chosen to have a decomposition of the dip in three basic colors. But this solution proved to be very rough and unsuited to in-line use.

The international application WO 99/66117 discloses a portable monitoring system which can be connected to an existing dyeing machine whenever monitoring of the dye dip becomes necessary. This device must be inserted along the circulation loop of the dyeing machine and the spectroscopic analysis of the dye dip takes place continuously on the liquid flowing along the circulation loop as long as the system is arranged therein.

The general purpose of the present invention is to remedy the above mentioned shortcomings by making available a dyeing machine which would perform measurement of the dyestuff concentrations in the dip during normal processing and take the necessary corrective measures as required.

In view of this purpose it was sought to provide in accordance with the present invention a dyeing machine comprising a container in which products to be dyed are placed, a source of coloring liquids adding liquids on command into the container to realize a dye dip, a unit to circulate the dye dip with respect to the product, spectroscopic analysis means to perform a spectroscopic analysis on the liquids and an electronic control and calculation device receiving the spectroscopic analysis data and calculating therefrom the concentrations of the various dyes in the dip on the basis of previously memorized spectroscopic information for the individual dyes, characterized in that the spectroscopic analysis means comprise a sampling and analysis device, which during the dyeing process automatically takes liquid samples from the container to a reading cell, at intervals, and performs a spectroscopic analysis on the taken samples in the reading cell.

Figure 2:
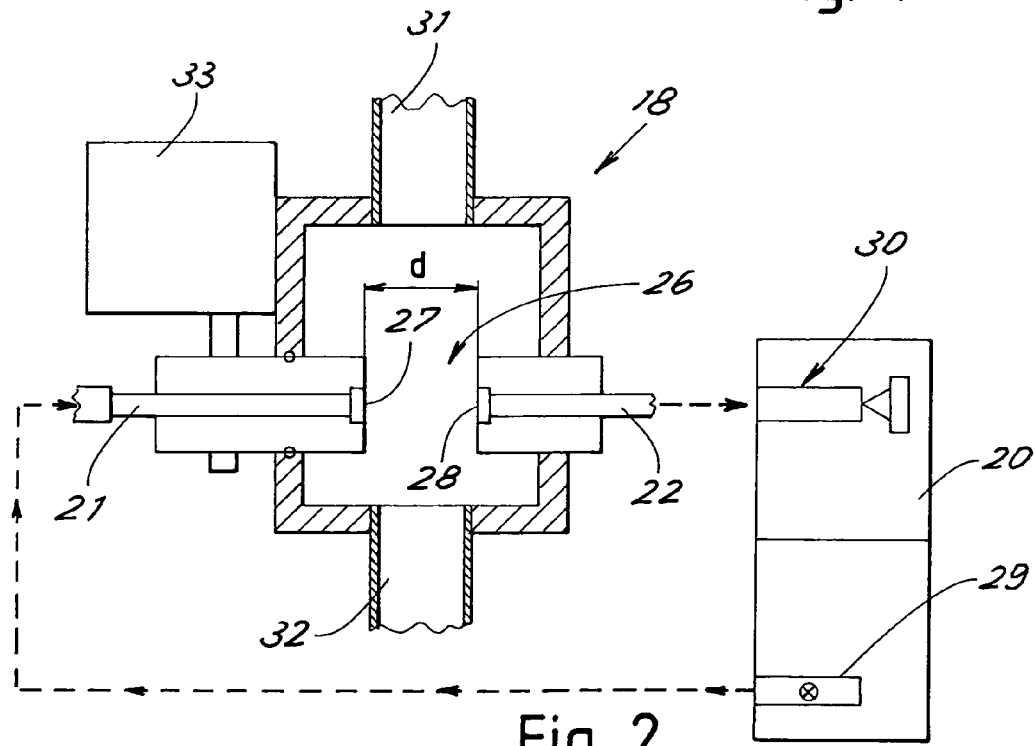

To clarify the explanation of the innovative principles of the present invention and its advantages compared with the prior art there is described below with the aid of the annexed drawings a possible embodiment thereof by way of non-limiting example applying said principles. In the drawings:

FIG. 1 shows a diagrammatic view of a machine in accordance with the present invention, and FIG. 2 shows a diagrammatic view of a detail of the machine of FIG. 1.

With reference to the figures, FIG. 1 shows a textile products dyeing machine designated as a whole by reference number 10 and comprising a container 11 pressurized or not in which are placed the products to be dyed in the form of yarn, loose textile fiber, mouse ribbon or tow or bolts of cloth wound or not on cones or supports depending on the requirements of the prior art. A known liquid dyestuffs source 12 inputs on command into the container the liquids to prepare a desired dye dip which is held in circulation with respect to the product by means of a purposeful circulation unit 13, for example a pump or a product handling system.

A sampling and analysis device 14 is connected to the container to take samples of the liquid in the container at intervals and perform a spectroscopic analysis thereon. The analysis device 14 sends the analysis data to an electronic control and calculation device, for example an appropriately programmed personal computer which after receiving the spectroscopic analysis data calculates therefrom the concentrations of the various dyestuffs in the dip on the basis of previously memorized spectroscopic information on the individual dyestuffs. This information may have been supplied or purchased separately.

The device 14 can be limited to memorizing in a memory 16 the data on the evolution of the dip concentrations for future use or can even compare the concentrations with the depletion behavior of the dip preset for reference and take action on parameters of the process through appropriate known actuators 34 (heaters, pH correctors) and by varying the dip circulation speed so as to control the absorption of the various dyestuffs by the product. For example, by reducing dip temperature, dyestuff absorption can be slowed. Corrections of the dyeing process behavior can be performed automatically this way.

To expand the information on the evolution of the process the machine can also comprise known sensors 17 for detection of various preselected physical magnitudes of the dip.

The device 15 can correlate the measurements of the sensors 17 with the dyestuff concentrations calculated starting from the spectroscopic analysis and memorize the correlations for future analysis and optimization of the process. For example, it might be sensed that a dyestuff is not absorbed well when the dip temperature exceeds a certain value and this could serve to optimize the behavior of temperatures in the future. The physical magnitudes detected by the sensors can advantageously comprise the temperature and pH of the dip, the speed of the recirculating pump, salinity et cetera. Correlations can also be established between the behavior of the concentrations and the addition of additives—for example, salts—so as to optimize the times of addition of these additives to the dip.

It is also very important to be able to appreciate the different profiles of depletion of the specific dyestuffs in the dye dip with variation in the surrounding parameters and the dyestuffs.

The sensors can also act as feedback for accurate control of the actuators 34.

The spectroscopic analysis device comprises a reading cell 18, a suction device 19 which fills the cell with the liquid taken from the container 11, and a spectrophotometer 20. Advantageously the sampling device is a syringe device which sucks the liquid through the cell to then return it into the container 11 after measurement. This avoids waste of liquid even with high measurement frequency.

The analysis device can also comprise circulation of washing liquid, advantageously water or having an aqueous base with appropriate additives, which could be added on command through a valve 23 (to replace the dyestuff liquid intercepted by a valve 24) and drained through a valve 25. Thus it is possible to ensure that in the reading cell there remains no residue capable of affecting the measurements.

In addition, the water coming from the outside is necessary for calibration of the device. The spectrophotometer has high resolution in the visible and is advantageously connected by optical fibers 21,22 to the reading cell 18. FIG. 2 shows diagrammatically in greater detail an advantageous embodiment of the reading cell 18. As may be seen in the figure, the reading cell has a passage 26 for the liquid between one light emitting surface 27 and a reading surface 28. The surface 27 is connected through the optical fiber 21 to an appropriate light source 29 while the facing reading surface 28 is connected through the optical fiber 22 to the sensor 30 of the spectrophotometer. One end of the passage 26 is connected through a duct 31 to the dip container while the other end of the passage is connected through a duct 32 to the controlled suction device 19. The detected measurement light passes thus through the liquid thickness which is formed between the two faces 27 and 28 after the passage from the spectrophotometer which performs the spectroscopic analysis.

The gauge 'd' of the reading passage 26 can be changed with precision by means of the controlled movement of the surface 27 by an actuator 33, for example a stepping motor. In this manner, before each measurement the control device 15 can adjust the gauge 'd' for measuring on the spectrophotometer a peak of absorbance included between minimum and maximum values predetermined to be optimal for correct measurement. Thanks to the changeable optical path it is possible to perform the readings in the entire range of concentrations which might be of interest by adopting the best reading conditions of the instrument based on the behavior in absorbance of the signal and in particular on the peak values.

Indeed, instrumental analysis of concentrations with a spectrophotometer is based on the well known law of Lambert and Beer which is applicable within a certain range of absorbance proportionate to the dyestuff concentration. At high dyestuff concentrations, in addition to leaving the linearity range, instrumental reading problems can arise because of the low signal and resulting possible confusion with the instrument's background noise. In the prior art of laboratory analysis it is necessary to perform a dilution and enter the resulting ratio in the calculation. This system would however be too costly to apply in an in-line automatic measurement since it is extremely difficult to obtain accurate dilutions automatically. There would also be a loss of dip since it is not possible to add the sample again at the cost of changing the dip ratio or having unacceptable loss of dyestuff in small machines.

In the machine in accordance with the present invention all this is avoided by using a variable step reading probe allowing the use of reading gauges of a magnitude inversely proportionate to the absorbance or proportionate to the transmittance (dyestuff concentration) of the dip.

The passage gauge is variable in a range between 0 and 25 mm and advantageously between 0 and 10 mm with steps around 0.01 mm or even less.

The difficulty of determining the size of the gauge because of the however limited mechanical construction inaccuracies of the probe give as a result an effective minimum absorbance value different from 0 and different from one instrument to another when the distance 'd' is reduced to the minimum possible quantity, i.e. when the actuator 33 is operated to take the surfaces 27,28 toward mutual contact. To avoid this, a special system allowing calculation of this space and bringing back the values read to the nominal calculation values was defined. The corrected values are used to set the optimal reading step by starting the stepping motor. The reading can always be performed automatically this way in an optimal manner.

Since for equal liquid the relationship between absorbance and gauge is linear, to compensate for the residual space the actuator 33 is controlled by the electronic control and calculation device 15 to perform measurements on the same liquid for different 'd' gauges, for example between 0 mm and 1 mm, which must give a straight line in the absorbance-gauge graph. If the gauge 0 does not correspond to the actual contact of the surfaces 27,28 the resulting straight line will not pass through the zero but will intersect the axis of the gauges at a negative point corresponding to the residual gauge which can thus be calculated, memorized and used by the electronic device to compensate for the normal measurements.

This results in an indirect optical manner of calculating a mechanical gauge otherwise difficult to evaluate because of its possible scantiness and because it is important to evaluate it with the probe assembled.

Correct calculation of this parameter always influences the results of the measurements progressively more as the measurement gauge decreases.

The parameter memorized by the electronic device remains linked to the specific measurement device.

It is now clear that the preset purposes have been achieved. During operation the machine will perform a dyeing cycle while the detected and possibly recorded data will be processed in the device 15 to find the data on concentration of the dyestuffs in the dip. The correlation of dyestuff concentrations with time, temperature, pH, salinity, pump flow rate (in dip circulation equipment) or material recirculation speed (in equipment with the goods moving), supplies data on the rising dynamics of the dyestuffs on the material being dyed (dip depletion). In addition, calculations covering the full range of wavelength measurement of the spectrophotometer with the squared minimums method as an alternative to or in combination with calculation based on neural or similar networks can be used. The system is very accurate and reliable compared with for example prior art proposals where it is attempted to analyze the liquid by means of simple colored filters.

The data taken and calculated can be used for optimization of future processing or for changing dip parameters in real time. The control device can then even take action on the process parameters by means of the above mentioned appropriate actuators 34.

With the machine in accordance with the present invention it is possible to adjust and optimize the rise of the dyestuffs on the products to be dyed while optimizing processing times, dyeing uniformity and control of dyestuff quantities drained into the sewage et cetera. It is also possible to optimize the rise of the dyestuffs on the material to be dyed by changing one of more process variables. It is also possible to have accurate indication of dip depletion and the percentages of each dyestuff of the formula with each reading.

Sampling of the concentration measurements can be performed with high frequency with resulting identification of deleterious transients for the correctness and quality of the dyeing process and with the capability of fast, accurate action during the process.

All this would be impossible with the costly prior art operations of dye dip sampling, laboratory control and the resulting loss of the dip portion taken. Loss of dip and the need for a long laboratory tie up among other things make possible in practice only a limited number of samplings and analyses for each processing cycle and, in any case, the resulting data can serve if at all for improvement of subsequent processing but not as self-adjustment of the cycle underway.

Naturally the above description of an embodiment applying the innovative principles of the present invention is given by way of non-limiting example of said principles within the scope of the exclusive right claimed here. For example, depending on the specific dyeing processes the machine could comprise appropriate additional members and known devices for the performance of such processes.

The invention claimed is:

1. Dyeing machine comprising:
a container (11) in which products to be dyed are placed;
a source (12) of coloring liquids adding liquids on command into the container to realize a dye dip;
a unit (13) to circulate the dye dip with respect to the product;
spectroscopic analysis means to perform a spectroscopic analysis on the liquids and an electronic control and calculation device (15) receiving the spectroscopic analysis data and calculating therefrom the concentrations of the various dyes in the dip on the basis of previously memorized spectroscopic information for the individual dyes;
characterized in that the spectroscopic analysis means comprise a sampling and analysis device (14), which during the dyeing process automatically takes liquid samples in the container to a reading cell (18), at intervals, and performs a spectroscopic analysis on the taken samples in the reading cell (18); and
characterized in that the sampling and analysis device (14) comprises a reading cell (18) having a passage (26) for the liquid with controlled variable gauge (d) and through said gauge (d) is made to pass a measuring light detected, after the passage, by a spectrophotometer (20) sending the data to said electronic device (15) which performs the spectroscopic analysis for calculation of the concentrations.

2. Machine in accordance with claim 1, characterized in that the sampling and analysis device (14) has an analyzed samples drain connected to the container (11) to return the samples into the container.

3. Machine in accordance with claim 1, characterized in that before each measurement the gauge (d) of said passage (26) in the reading cell (18) is adjusted on command by the electronic device (15) to detect at the spectrophotometer outlet an absorbance peak included between the predetermined maximum and minimum values.

4. Machine in accordance with claim 1, characterized in that the passage gauge (d) is adjusted on command to have a reading gauge of a magnitude inversely proportionate to the liquid absorbance.

5. Machine in accordance with claim 1, characterized in that the passage gauge (d) is variable in a range included between 0 mm and 25 mm with steps around 0.1 mm.

6. Machine in accordance with claim 1, characterized in that the passage (26) in the reading cell (18) is connected on one side to said container (11) and on the other side to a controlled suction device (19) for sucking liquid from die container to the cell and vice versa.

7. Machine in accordance with claim 6, characterized in that the suction drive (19) is a syringe aspirator.

8. Machine in accordance with claim 1, characterized in that it comprises dip physical magnitude detection sensors (17) whose measurements are sent to an electronic device (15) which correlates said measurements with the concentrations calculated by the spectroscopic analysis.

9. Machine in accordance with claim 8, characterized in that the physical magnitudes detected include one or more magnitudes chosen from among temperature, pH and salinity of the dip and speed of circulation of the dip with respect to the product 10. Machine in accordance with claim 1, characterized in that the electronic device (15) which receives the spectroscopic analysis data and calculates therefrom the concentrations of the various dyestuffs in the dip compare the calculated concentrations with a preset behavior in time and commands dyeing parameters on the basis of the results of the comparison.

11. Machine in accordance with claim 10, characterized in that the dyeing parameters include one or more magnitudes chosen from among temperature, pH and salinity of the dip and circulation speed of the dip with respect to the product.

12. Machine in accordance with claim 1, characterized in that during a calibration phase of tile spectroscopic analysis device (20) said device is commanded by the electronic control and calculation device (15) to perform a series of measurements of absorbance of the liquid with different gauge (d) of said passage (26) with the electronic device (15) calculating a gauge-absorbance line identified by the series of measurements and memorizing as residual gauge the intersection of said line with the axis of the gauges with the residual gauge being subsequently used by the electronic device for correcting the gauges used in subsequent measurements.

13. Machine in accordance with claim 12, characterized in that the washing liquid is water or water based with additives.

14. Machine in accordance with claim 1, characterized in that during a calibration phase of the spectroscopic analysis device (20) said device is commanded by the electronic control and calculation device (15) to reduce to the minimum the gauge (d) of said passage (26) and measure the absorbance of a liquid remaining in the residual gauge with said absorbance measurement being memorized by die electronic device (15) and used subsequently for correcting the subsequent measurements by said residual gauge.

15. Machine in accordance with claim 1, characterized in that it comprises a circuit (23, 25) for controlled inlet and extraction of a washing liquid in the reading cell (18).

* * * * *